United States Patent
Bosy et al.

(10) Patent No.: US 10,324,025 B2
(45) Date of Patent: Jun. 18, 2019

(54) OPTICAL FLOW CELL AND TEST HEAD APPARATUS

(71) Applicant: Instrumentation Laboratory Company, Bedford, MA (US)

(72) Inventors: Brian Joseph Bosy, Hull, MA (US); Josef Kerimo, Concord, MA (US)

(73) Assignee: Instrumentation Laboratory Company, Bedford, MA (US)

( * ) Notice: Subject to any disclaimer, the term of this patent is extended or adjusted under 35 U.S.C. 154(b) by 0 days.

(21) Appl. No.: 15/971,061

(22) Filed: May 4, 2018

(65) Prior Publication Data

US 2018/0252633 A1 Sep. 6, 2018

Related U.S. Application Data

(62) Division of application No. 15/134,528, filed on Apr. 21, 2016, now Pat. No. 9,976,946.

(51) Int. Cl.
*G01N 21/01* (2006.01)
*G01N 21/05* (2006.01)
(Continued)

(52) U.S. Cl.
CPC .............. *G01N 21/05* (2013.01); *B01L 3/508* (2013.01); *G01N 21/0303* (2013.01);
(Continued)

(58) Field of Classification Search
CPC ........................ B01F 17/0028; B01F 17/005; B01F 17/0064; B01L 2400/084; B01L 3/0241;
(Continued)

(56) References Cited

U.S. PATENT DOCUMENTS 5,351,686 A 10/1994 Stever et al.
6,172,744 B1 1/2001 Scharlack et al.
(Continued)

FOREIGN PATENT DOCUMENTS

DE 102014000056 5/2015
EP 1950569 7/2008
(Continued)

OTHER PUBLICATIONS

International Search Report and Written Opinion of corresponding PCT Application No. PCT/US2018/045969, dated Aug. 9, 2018, 13 pages.
(Continued)

*Primary Examiner* — Sunghee Y Gray
(74) *Attorney, Agent, or Firm* — Burns & Levinson, LLP; Joseph P. Quinn

(57) ABSTRACT

A sample cell apparatus for use in spectroscopic determination of an analyte in a body fluid sample includes a first plate member made from an optically clear material and a second plate member made from an optically clear material and opposing the first plate member. A channel extending into a surface of the first plate member and an opposing surface of the second plate member houses a floating seal. The floating seal surrounds a fluid chamber that retains a sample of body fluid for optical measurement. The fluid chamber may be opened for flushing by separating the first plate member from the second plate member. During measurements the fluid chamber is closed to define a repeatable optical path-length therethrough by urging the first plate member against the second plate member without compressing the floating seal between the first plate member and the second plate member.

10 Claims, 9 Drawing Sheets

(51) Int. Cl.
  *G01N 21/03* (2006.01)
  *G01N 21/27* (2006.01)
  *G01N 33/49* (2006.01)
  *B01L 3/00* (2006.01)
  *G01N 21/11* (2006.01)

(52) U.S. Cl.
  CPC ......... *G01N 21/27* (2013.01); *G01N 33/4915* (2013.01); *B01L 2200/0689* (2013.01); *B01L 2300/0822* (2013.01); *G01N 2021/058* (2013.01); *G01N 2021/115* (2013.01); *G01N 2201/061* (2013.01); *G01N 2201/062* (2013.01); *G01N 2201/0668* (2013.01)

(58) Field of Classification Search
  CPC .......... B01L 3/502746; G01N 21/0303; G01N 21/05; G01N 21/27; G01N 2201/061; G01N 2201/062; G01N 27/44752; G01N 33/4915; Y10T 436/25; Y10T 436/2525; Y10T 436/25625; Y10T 436/2575
  USPC ................................................. 356/244–245
  See application file for complete search history.

(56) References Cited

U.S. PATENT DOCUMENTS

| | | | |
|---|---|---|---|
| 6,188,474 B1 | 2/2001 | Dussault et al. | |
| 6,262,798 B1 | 7/2001 | Shepherd et al. | |
| 2001/0048899 A1 | 12/2001 | Marouiss et al. | |
| 2006/0203249 A1* | 9/2006 | Liu | G01N 21/0303 356/440 |
| 2009/0178495 A1* | 7/2009 | Steigmiller | C12M 33/04 73/863.72 |
| 2012/0177543 A1 | 7/2012 | Battrell et al. | |
| 2012/0218551 A1 | 8/2012 | Born | |
| 2014/0004548 A1* | 1/2014 | Gordon | B01L 3/5029 435/21 |
| 2017/0113221 A1 | 4/2017 | Hoffman et al. | |

FOREIGN PATENT DOCUMENTS

| | | |
|---|---|---|
| EP | 1950569 A1 | 7/2008 |
| EP | 2026057 | 2/2009 |
| GB | 796745 A | 6/1958 |
| GB | 2071355 A | 9/1981 |
| GB | 2349349 | 11/2000 |
| JP | 2008-216094 | 9/2008 |
| WO | 2009-062667 | 5/2009 |
| WO | 2009062667 A1 | 5/2009 |
| WO | 2017184399 A1 | 10/2017 |

OTHER PUBLICATIONS

Communication Relating to the Results of the Partial International Search of corresponding PCT Application No. PCT/US2017/027151, dated Apr. 12, 2017, 15 pages.

International Search Report and Written Opinion of corresponding PCT Application No. PCT/US2017/027151, dated Aug. 22, 2017, 23 pages.

International Preliminary Report on Patentability for Application No. PCT/US2017/027151, dated Oct. 23, 2018 (14 pages).

\* cited by examiner

OPTICAL FLOW CELL AND TEST HEAD APPARATUS

CROSS REFERENCE TO RELATED APPLICATION

This application is a divisional of U.S. application Ser. No. 15/134,528, filed on Apr. 21, 2016, and claims priority from it. This application is related to a co-pending continuation-in-part U.S. application Ser. No. 15/694,083, filed on Sep. 1, 2017. The entire content of the U.S. application Ser. No. 15/134,528 and U.S. application Ser. No. 15/694,083 are incorporated herein in their entireties by reference for all purposes.

FIELD OF TECHNOLOGY

Aspects of the present disclosure are directed to the field of spectroscopic determination of analyte content in a sample, and more particularly to the field of presenting a body fluid sample for spectroscopic analysis in an optical flow cell.

BACKGROUND

In a variety of clinical settings, it is important to measure certain chemical characteristics of blood, for example, the analytes Hemoglobin (e.g., Carboxyhemoglobin, Oxyhemoglobin, Methemoglobin), proteins, lipids, bilirubin. These settings range from a routine visit of a patient to a physician's office, an emergency room, or monitoring of a hospitalized patient, for example. Measurement of an analyte in a body fluid sample may be accomplished by numerous methods one of which is by spectroscopic determination.

Spectroscopic determination of analyte content in a body fluid sample, such as a blood sample for example, involves presenting the body fluid sample to a light source and analyzing properties of light transmitted through the sample or reflected from the sample. A structure for presenting a fluid sample in a spectroscopic measurement instrument such as a clinical analyzer is generally called an optical flow cell. In certain implementations, a sample chamber in the sample cell is preferably configured with a precise depth dimension during measurements so that a path-length of light through the sample is predetermined. The optical path-length through an optical flowcell may preferably be maintained within a few microns during a measurement, for example. Following a measurement, the sample may be flushed from the flow cell to prepare for analysis of another sample. During the flushing process the optical flow cell may be opened or partially opened for more efficient flushing, for example.

Two alternative sample cell configurations for optical spectroscopy as previously known are described in U.S. Pat. No. 6,188,474. In one configuration, a previously described sample cell is selectively adjustable between a first position having a predetermined optical path-length adapted for analyte measurement while the sample is in the measurement zone, and a second position having a predetermined other path-length adapted for clearing the sample from the flow path. This previously known sample cell includes two cell portions that are maintained in a slidable fluid tight engagement with one another so that adjustability of the fluid flow path from a small cross section flow path for measurement to a larger cross section flow path for flushing is accomplished by sliding the mating surfaces relative to another. The slidable engagement in this configuration detrimentally may trap sample portions between the first cell portion and the second cell portion which may cause contamination to a sample under measurement and may affect the dimensional consistency of the path-length. In another configuration, the previously described sample cell is selectively adjustable between a first position having a predetermined optical path-length for measurement and a second position for clearing the sample by applying and relaxing a compressive force between the first cell portion and the second cell portion. In this configuration, the path-length may be detrimentally affected by compression of an elastomeric gasket between the first cell portion and a second cell portion.

SUMMARY

Aspects of the present disclosure include a variable path length optical flow cell such as the type of optical flow cell used for measuring an analyte in a clinical analyzer. The analytes are typically found in a body fluid including but not limited to blood, plasma and serum. Analytes measured in optical flow cell include but are not limited to Hemoglobins, proteins, lipids, and bilirubin, for example. The disclosed flow cell expands and closes like a bellows to achieve a first depth for cleaning and a shallower second depth for measurement. In one embodiment, sealing in the disclosed flow cell is achieved by a diamond shaped seal surrounding an inner fluid chamber. The diamond shaped seal is operative to seal the inner fluid chamber by expanding laterally against walls of a seal channel containing the seal in the flow cell throughout the movement of the two portions of the optical flow cell. The seal is not compressed between the first portion of the cell and the second portion of the cell. This improves precision and repeatability of an optical path-length through the flow cell.

BRIEF DESCRIPTION OF THE DRAWINGS

The foregoing will be apparent from the following more particular description of example embodiments of the present disclosure, as illustrated in the accompanying drawings in which like reference characters refer to the same parts throughout the different views. The drawings, which are not necessarily to scale, emphasis illustrative embodiments of the present disclosure.

DETAILED DESCRIPTION

Figure 1A:
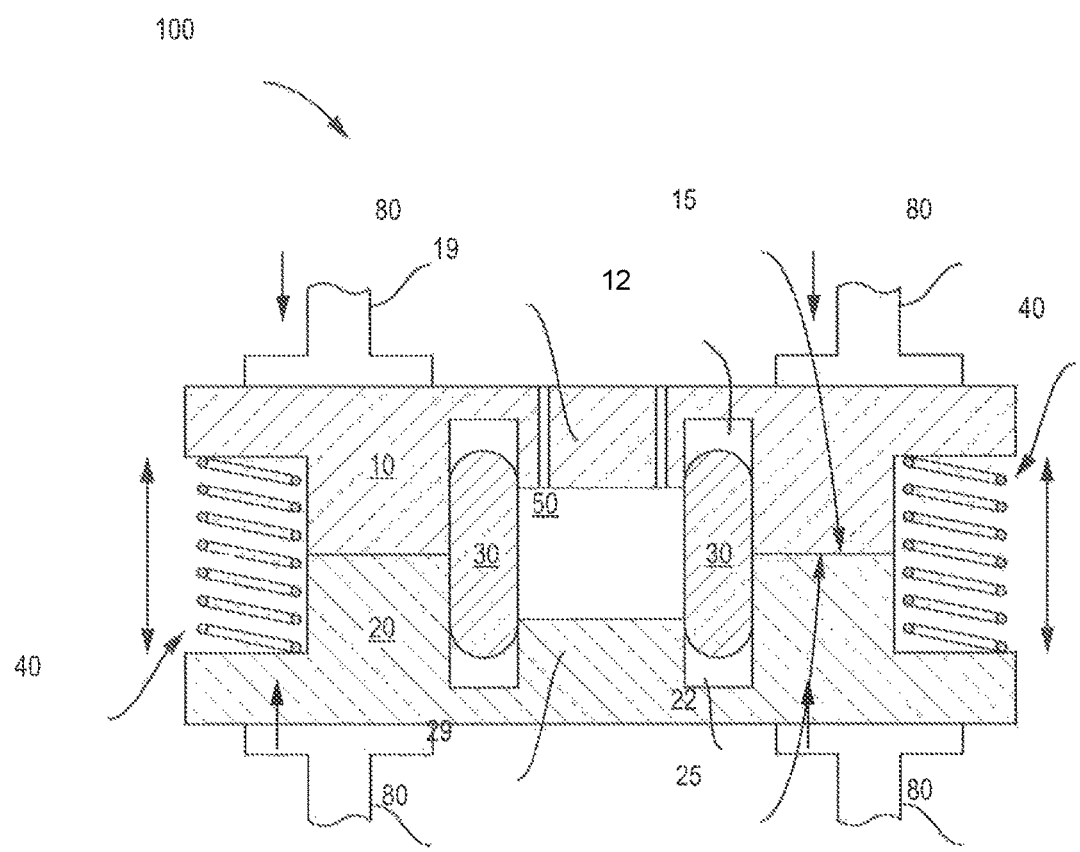
FIGS. 1A-1C illustrate an example of an optical flow cell according to an aspect of the present disclosure.

Aspects of the present disclosure include a variable path length optical flow cell for optical measurement of analytes in a body fluid sample in a clinical analyzer such as but not limited to GEM 4000 and GEM 5000 clinical analyzers (Instrumentation Laboratory Company, Bedford, Mass.). In an embodiment, the disclosed flow cell closes to provide chamber having an optical path through the chamber having a path-length of about 80 micrometers to about 90 micrometers for optical determination of one or more analytes of a body fluid sample in the chamber. When the flow cell is in the closed configuration for sample analysis, the optical path-length through an upper portion of the flow cell and a lower portion of the flow cell is very accurate due to a very small tolerance of displacement between an upper portion of the flow cell and a lower portion of the flow cell. When a measurement is complete, the flow cell can be opened for washing out the body fluid sample from the sample chamber. When the flow cell is in the open configuration for cleaning, the tolerance of displacement between the upper portion of the flow cell and the lower portion of the flow cell is not critical and the gap between the upper portion and lower portion of the flow cell may be significantly greater than 80-90 micrometers. In an illustrative embodiment, when the flow cell is in the open configuration for wash out, gap between the upper portion of the flow cell and the lower portion of the flow cell may provide a chamber depth of about 250-400 micrometers, for example.

Aspects of the present disclosure include a floating seal surrounding the sample chamber. The seal is effective by lateral compression of the seal against sidewalls of a seal channel surrounding the sample chamber. Some extra space is provided above and below the seal in the seal channel. The extra space prevents the seal from being compressed vertically, or from bottoming-out to form face seal between the top portion and bottom portion of the sample cell.

Sample cell configurations that employ face seals do not exhibit repeatable measurement lengths within one micron tolerance. By avoiding compression of the seal between the top portion and bottom portion of the sample cell, the disclosed floating seal configuration allows the sample cell to be closed to a repeatable chamber height within about one micron. This closed chamber height provides an optical measurement distance that is accurate and repeatable within about one micron in a height range of about 0.09 mm in some embodiments to about 0.5 mm distance in other embodiments.

In an illustrative embodiment, closing of the disclosed flow cell may be actuated using low cost shape memory alloy such as nitinol, for example. Alternatively, the flow cell maybe closed by an actuation mechanism that includes a solenoid or an electric motor such as a stepper motor, for example. The flow cell halves are urged away from each other toward the open configuration by a spring force when the actuation mechanism is retracted or relaxed.

Figure 1B:
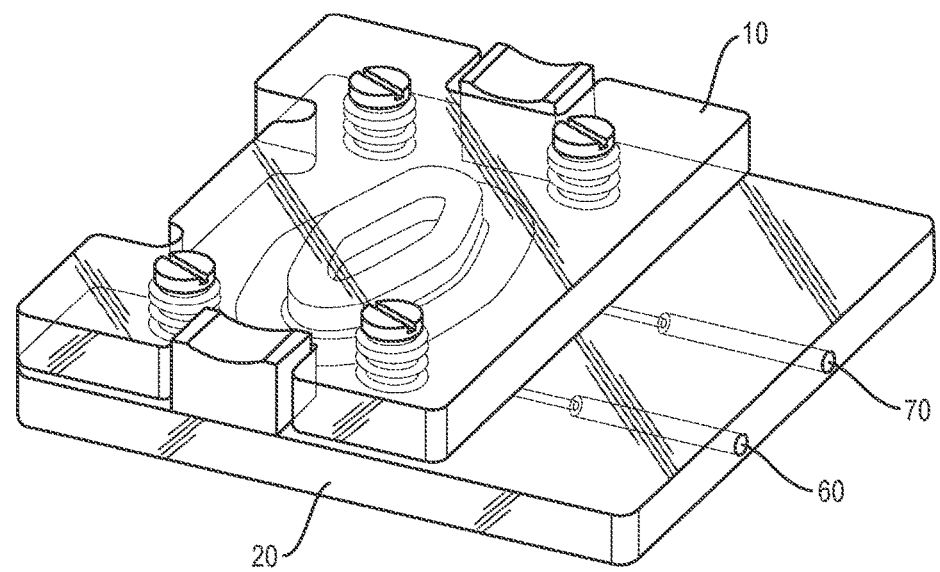
Figure 1C:
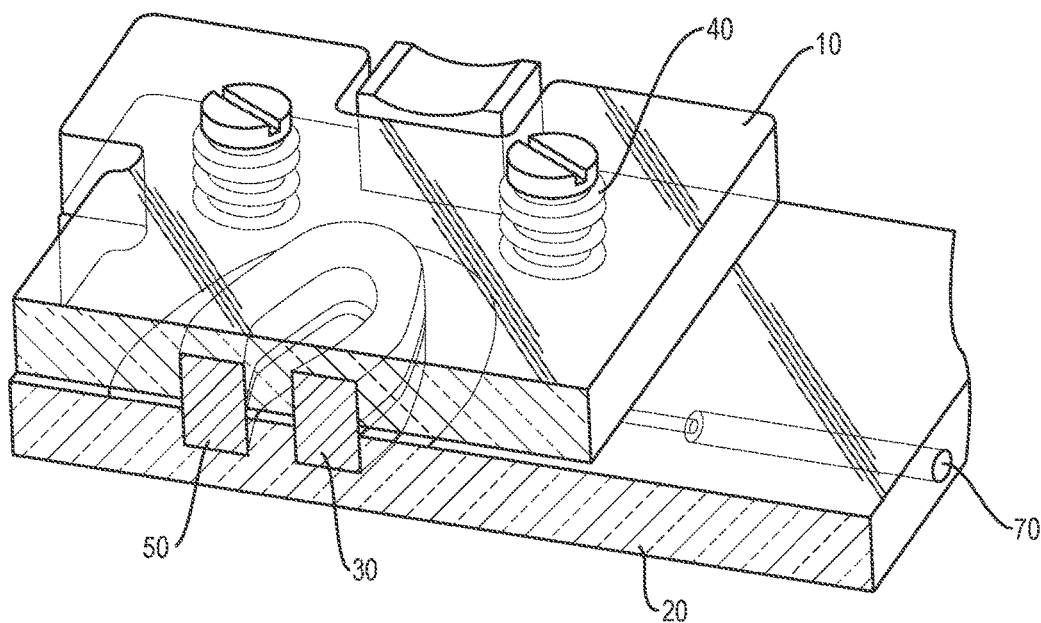

Referring to FIGS. 1A-1C, aspects of the present disclosure include a sample cell apparatus 100 for use in spectroscopic determination of an analyte in a body fluid sample. The sample cell apparatus 100 includes a first plate member 10 made from an optically clear material and a second plate member 20 made from an optically clear material and opposing the first plate member 10. A first surface of the first plate member 10 faces the second plate member 20. The first surface includes a first well portion 19, a first seal channel portion 12 adjacent to the first well portion 19, and a first abutment surface 15 outside of the first well portion 19 and outside of the first seal channel portion 12. A second surface of the second plate member 20 faces the first plate member 10. The second surface includes a second well portion 29 aligned with the first well portion 19 to form a sample chamber 50, a second seal channel portion 23 aligned with the first seal channel portion 12 and adjacent to the second well portion 29, and a second abutment surface 25 outside of the second well portion 29 and outside of the second seal channel portion 23 and aligned with the first abutment surface 15. The first well portion 19 has a fixed depth relative to the first abutment surface 15, and the second well portion 29 has a fixed depth relative to the second abutment surface 25. One or more spring members 40 are configured between the first plate member 10 and the second plate member 20 to urge the first plate member 10 away from the second plate member 20. A floating seal 30 extends into the first seal channel portion 12 and the second seal channel portion 22. The floating seal 30 is compressed transversely between sidewalls of the first seal channel and the second seal channel. According to an aspect of the present disclosure, the floating seal 30 defines a periphery of the sample chamber. A fluid inlet path 60 extends through the first plate member 10 or the second plate member 20 into the sample chamber 50. A fluid outlet path 70 also extends through the first plate member 10 or the second plate 20 into the sample chamber 50.

According to another aspect of the present disclosure, the sample cell apparatus 100 includes an actuator member 80 configured to controllably overcome the spring member(s) to urge the first plate member 10 against the second plate member 20 by a displacement defined by abutment between the first abutment surface 15 and the second abutment surface 25.

According to an aspect of the present disclosure, the actuator member 80 may include a shape memory member. The shape memory member may be made from nitinol, or another shape memory material, for example. According to another aspect of the present disclosure, the actuator member 80 may include an electric motor or a solenoid, for example.

According to another aspect of the present disclosure, the spring members 40 may be cantilever springs. The cantilever springs may be monolithically formed with the first plate member 10 and/or the second plate member 20, for example. According to another aspect of the present disclosure, the spring members may be compression springs, or the like.

In certain embodiments, the sample chamber 50 may be elongated. The inlet path 60 may be located proximate to a first end of the elongated sample chamber 50, and the outlet path 70 may be located proximate to a second end of the sample chamber 50 opposite the first end of the sample chamber 50. In certain embodiments, the sample chamber 50 and the floating seal 30 may be substantially diamond shaped.

According to an aspect of the present disclosure, a light source is directed through the first plate member 10 into the sample chamber 50. A light detector apparatus is directed to receive light from the light source that has passed through the first plate member 10, the sample chamber 50 and the second plate member 60.

In certain embodiments, the light detector apparatus may be a spectroscope, for example. The light source and/or the light detector may be integrated with actuator member.

According to an aspect of the present disclosure, the sample cell apparatus 100 may include an outer surface having a detent structure configured for engaging a mating detent structure in the actuator member 80 for locating the sample cell apparatus relative to the actuator member and/or relative to the light source and light detector apparatus.

Figure 2:
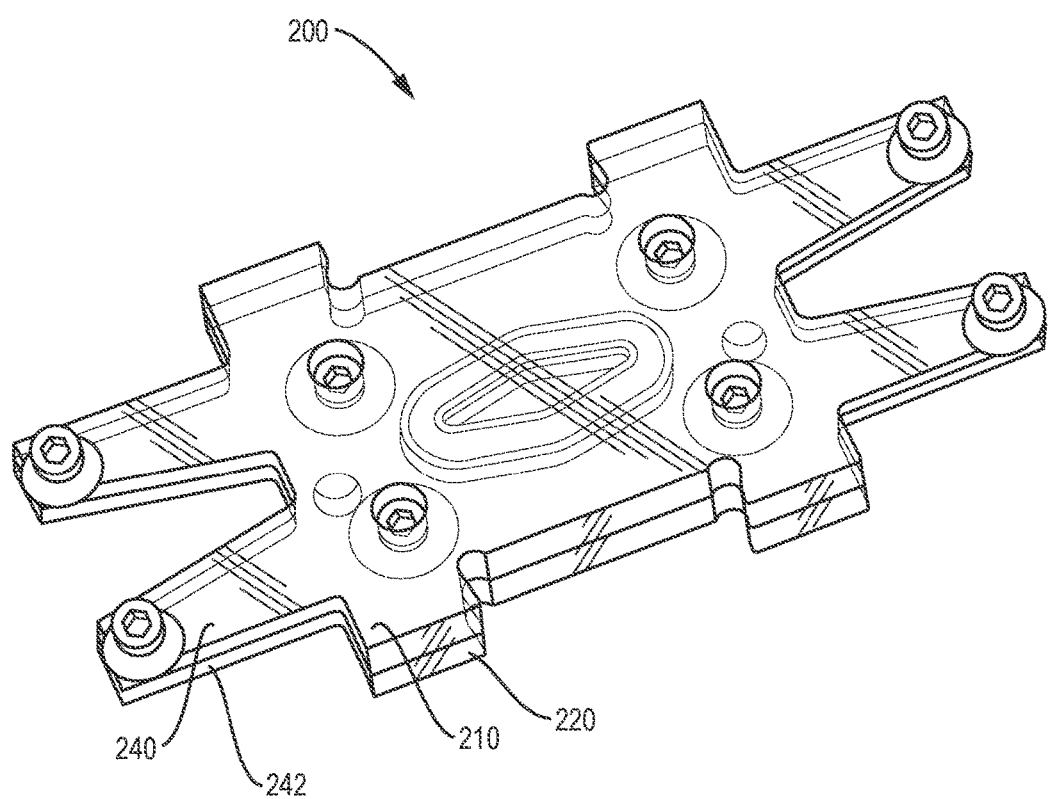
FIG. 2 illustrates an optical flow cell including cantilever arms configured to provide an opening force between portions of the optical flow cell according to an aspect of the present disclosure.

Referring to FIG. 2, in an illustrative embodiment of the disclosed flow cell 200, one or more finger portions 240, 242 are integrally molded with the first plate member 210 and the second plate member 220 respectively to form cantilever spring members configured to urge the first plate member 210 away from the second plate member 210. The cantilever spring members may be used instead of or in addition to compression springs (40 in FIGS. 1A-1C), for example. Because the gap dimension between the first plate member and the second plate member is not as critical while the flow cell 200 is in the open cleaning configuration as it is in when the flow cell 200 is in the closed measurement configuration, simple spring members such as the described cantilever spring arms are sufficient to meet design requirements for applying a separating force. Alternative embodiments may provide a spring force to separate the first plate member from the second plate member with compression springs or an elastomeric pad such as a foam rubber pad, or a combination of spring types, for example.

Figure 3:
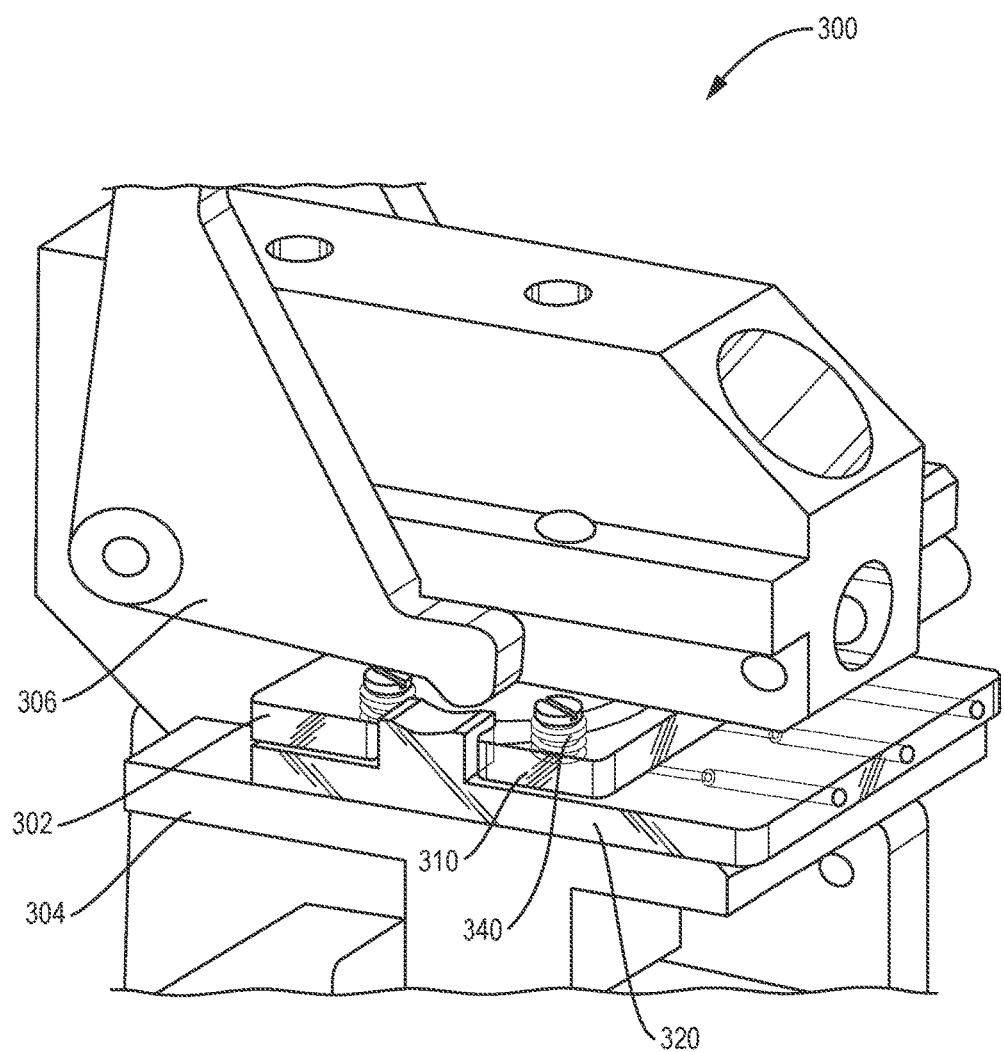
FIG. 3 illustrates a test head apparatus for locating and actuating an optical flow cell according to an aspect of the present disclosure.

Referring to FIG. 3, an embodiment of the disclosed flow cell 302 may be configured for removably mounting in a test head apparatus 300. The test head apparatus 300 may include a flow cell support structure 304 and an actuating member 306. The actuating member 306 is configured to controllably apply a force to the flow cell 302, which compresses the top portion 310 of the flow cell 302 against the bottom portion 320 of the flow cell by overcoming the separating force of the compression spring(s) 340. The actuating member 306 may be coupled to one or more mechanical actuators. Various types of mechanical actuators including, pneumatic actuators, hydraulic actuators, electric motors, are well known and may suitable for controllably driving the actuating member 360 in the test head apparatus, for example.

In an illustrative embodiment, the test head apparatus 300 may also include a light source configured for directing light though the test cell 302 and a spectrometer configured for receiving light from the light source that has passed through the test cell 302. The light source may include a neon light source and/or an LED light source for example. The spectrometer may include spectrometer optics and/or a diffuser, for example.

In another aspect of the disclosure, an optical diffuser may be integrally part of first plate member 10 and/or the second plate member 20 shown in FIGS. 1A-1C, for example. For example, a thin diffuser can be affixed to the plates or, alternatively, the surface of the plates can be frosted to diffuse the light.

Figure 4:
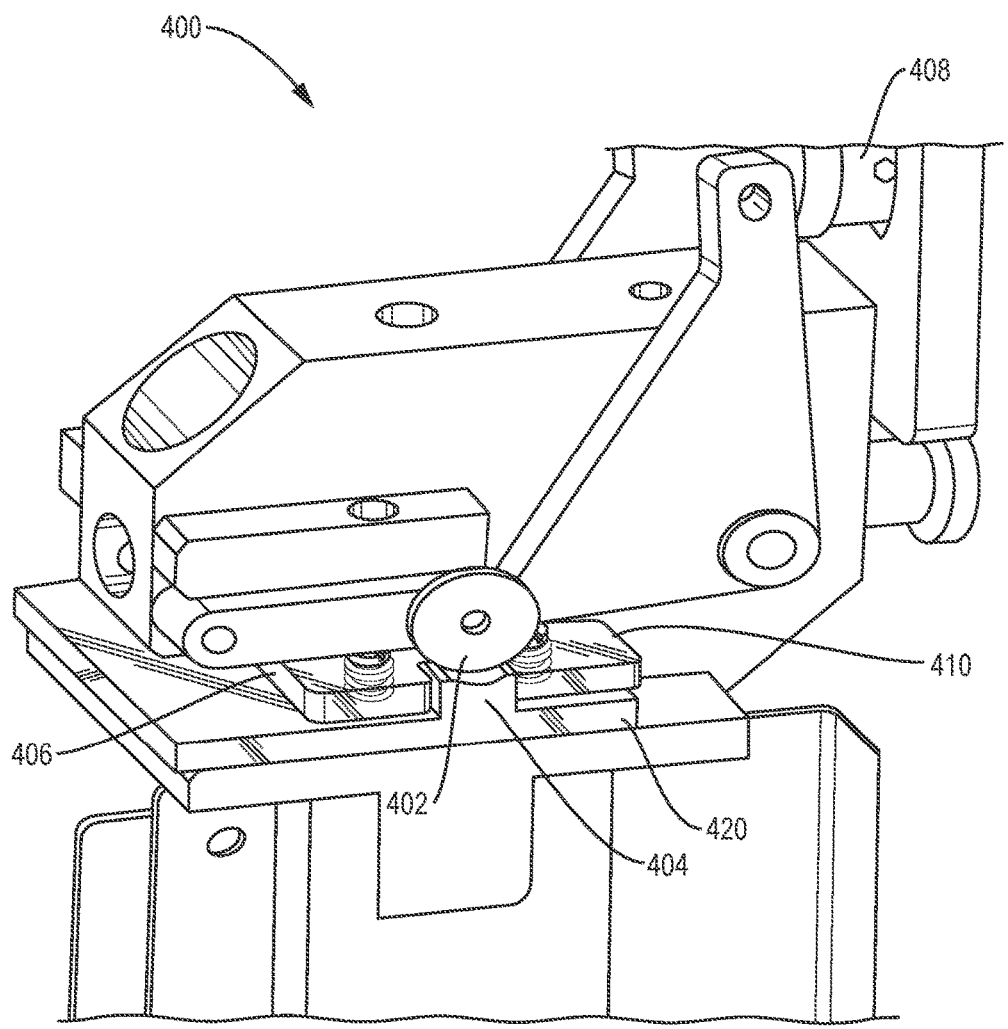
FIG. 4 illustrates a test head apparatus for locating and actuating an optical flow cell according to another aspect of the present disclosure.

Referring to FIG. 4, according to an aspect of the present disclosure, the disclosed flow cell 406 may include an alignment portion 404 for aligning the flow cell properly when it is mounted in the test head apparatus 400. The alignment portion 404 may include a depression or detent in the surface of the top portion 410 or bottom portion 420 of the flow cell 406. The alignment portion 404 is configured for engaging an alignment and retention portion 402 of the test head apparatus 400. In an illustrative embodiment, the alignment and retention portion 402 may include a wheel configured to sit in the depression/detent of the alignment portion 404 of the flow cell 406 when the flow cell 406 is properly located in the test had apparatus 400. The wheel may be spring biased against the alignment and retention portion 402 of the flow cell 406, for example.

Figure 5:
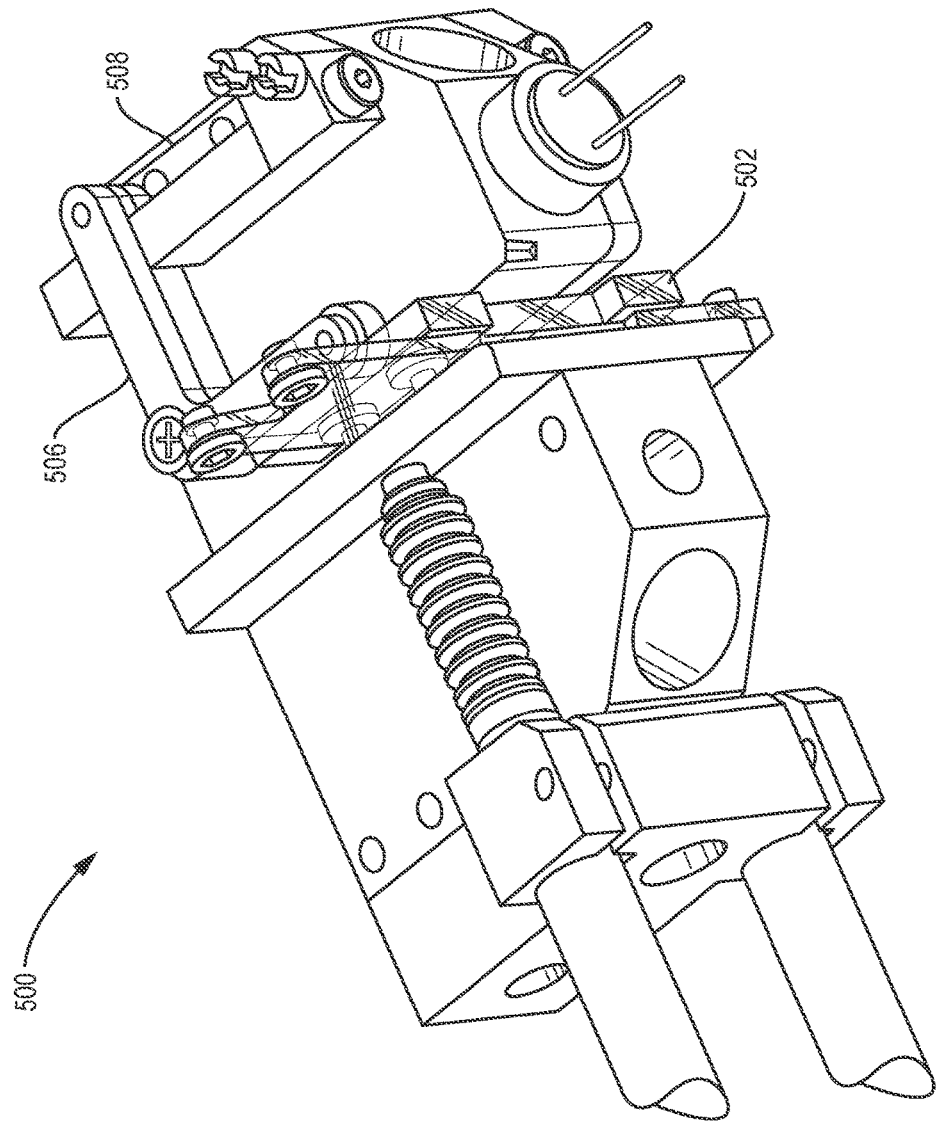
FIG. 5 illustrates a test head apparatus for locating and actuating an optical flow cell according to another aspect of the present disclosure.

Referring to FIG. 5, an embodiment of the disclosed test head apparatus 500 includes an actuating member 506 operatively coupled to a nitinol wire 508. The nitinol wire changes length upon application of electrical energy applied to the nitinol wire, and returns to an original length upon removal of the electrical energy. This shape memory characteristic of the nitinol wire enables a simple and reliable electro-mechanical actuation mechanism for controlling movement of the actuating member 506 by applying and removing a voltage and/or electrical current to the nitinol wire.

Figure 6:
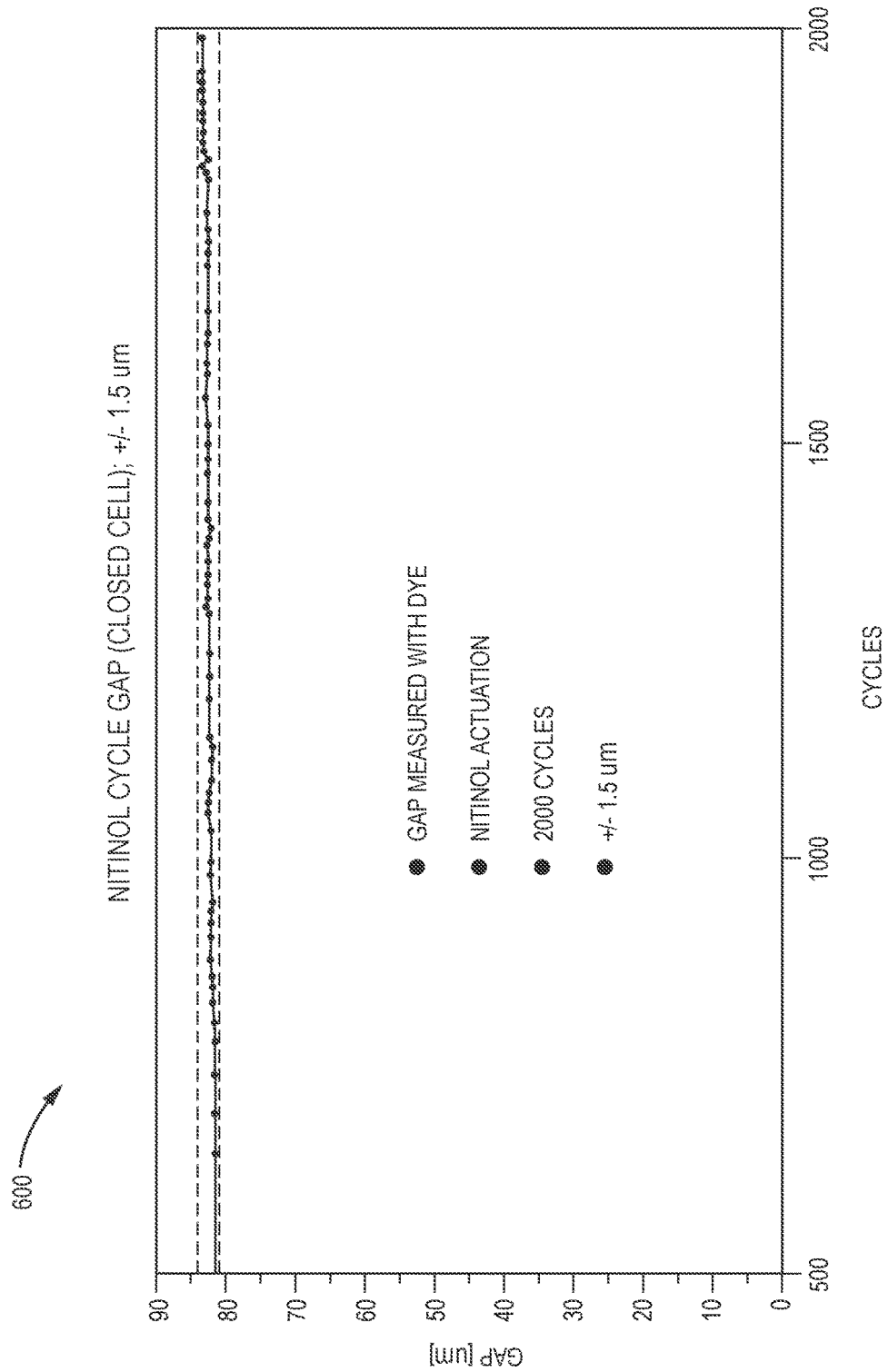
FIG. 6 is a graph of test data illustrating optical path length repeatability in a test head apparatus according to an aspect of the present disclosure.

FIG. 6 is a graph 600 of test data including measurements of the optical path length through a flow cell 502 using an embodiment of the test head apparatus as shown in FIG. 5 in which actuation was implemented by energizing the nitinol wire 508. In this configuration the gap was repeatable with +/−1.5 microns.

In previously known optical test heads, a light detector portion of a spectrometer device has typically been mounted in the test head and connect to an external portion of the spectrometer with a fiber optic cable. This adds cost and complexity to the test head apparatus. Aspects of the present disclosure include an optical light engine integrated in a test head apparatus. The disclosed integrated optical light engine combines a light emitting diode (LED), a neon lamp source, a spectrometer, optics with diffuser, and a mechanism for actuating a variable path length flow cell. The disclosed test head apparatus head is compact and rugged and avoids optical fibers for coupling the LED and spectrometer to the test head. The integrated optical head enables portable blood gas instruments to be constructed with lower costs and greater simplification, for example.

Figure 7:
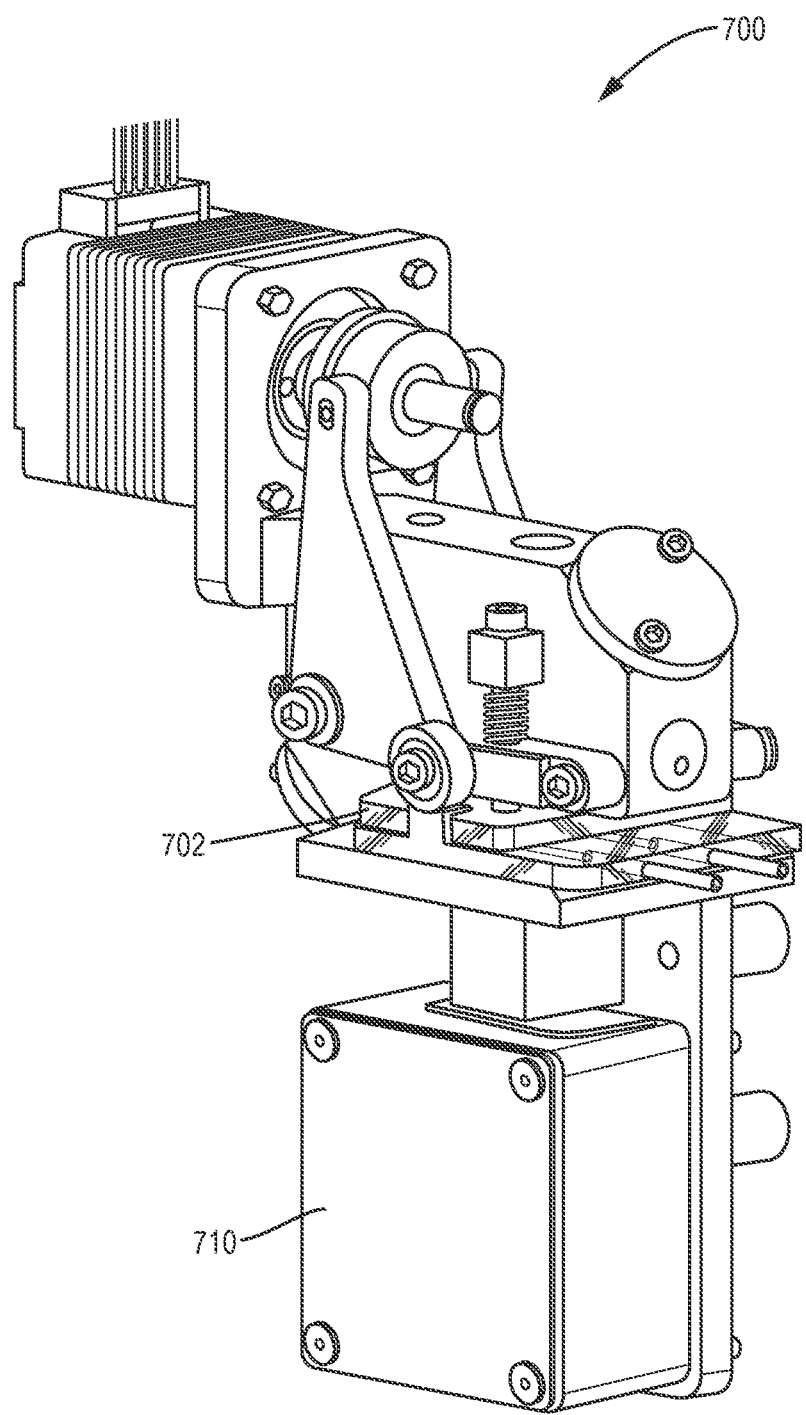
FIG. 7 illustrates a test head apparatus for locating and actuating an optical flow cell according to another aspect of the present disclosure.

In one example, disclosure, a small spectrometer, such as modular spectrometer by Ocean Optics, Inc. of Dunedin, Fla., USA, may be mounted in the test head and directly coupled to external processing equipment, for example without employing fiber optic cables. An illustrative embodiment of the disclosed test head apparatus 700 as shown in FIG. 7, includes a spectrometer 710, such as spectrometer model STS by Ocean Optics, Inc., mounted directly in the test head apparatus 700. The spectrometer 710 is configured for analyzing light that is transmitted through a flow cell 702 mounted in the test head apparatus 700. The disclosed configuration including an incorporated spectrometer 710 in the test head apparatus 700 is significantly less expensive than previously known test head configurations that couple a spectrometer light detector portion to a spectrometer device with expensive fiber optic cable bundles, for example.

Figure 8:
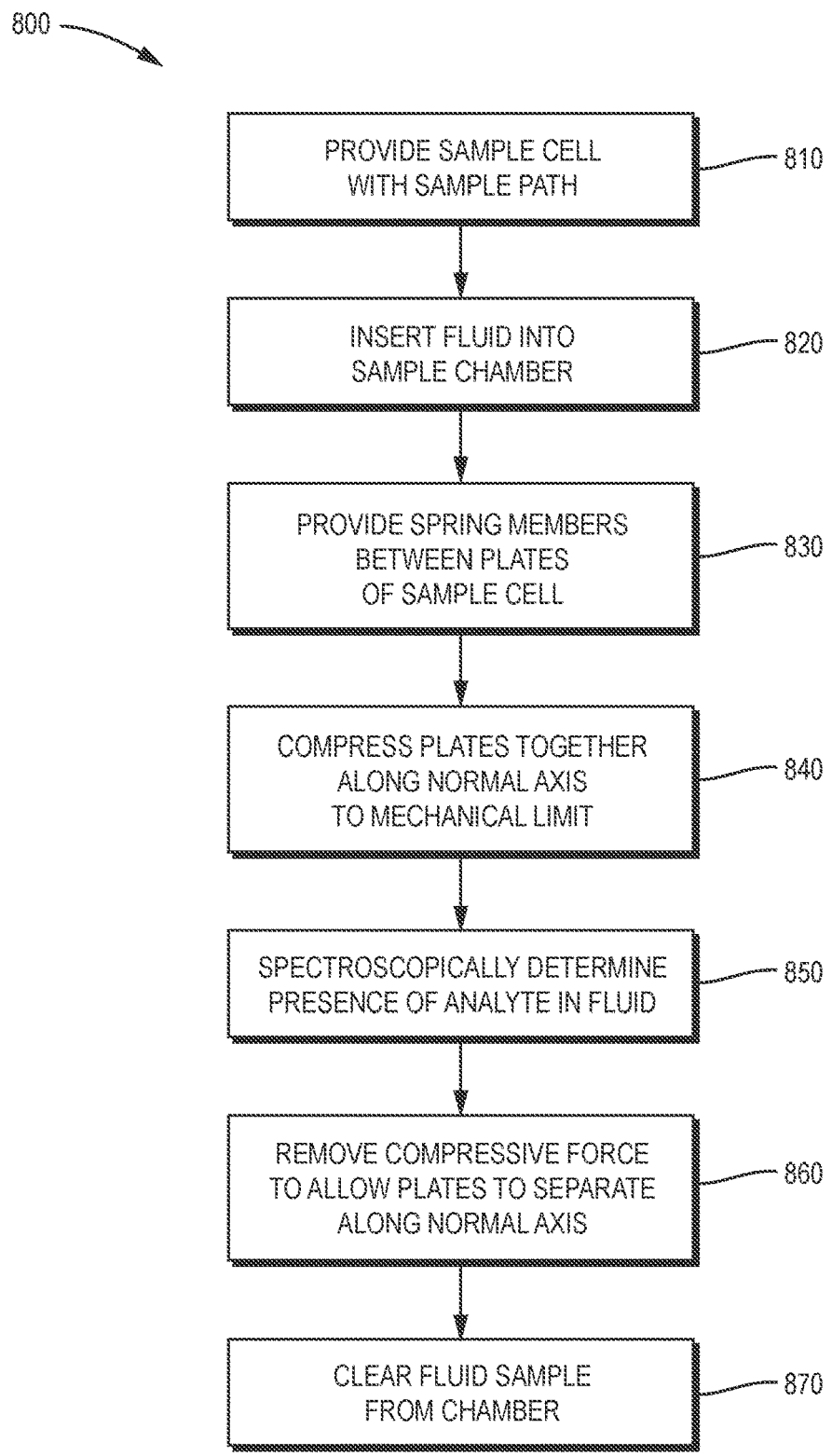
FIG. 8 is a process flow diagram describing a method for spectroscopic determination of an analyte in a body fluid sample, according to an aspect of the present disclosure.

Referring to FIG. 8, another aspect of the present disclosure includes a method 800 for spectroscopic determination of an analyte in a body fluid sample. At block 810, the method 800 includes providing a sample cell having a sample path extending between a first plate member and an opposing second plate member. The sample path is adapted for communicating the body fluid sample from a fluid inlet path through a sample chamber between the first plate member and the second plate member to a fluid outlet path. At block 820, the method includes inserting the body fluid sample into the chamber. At block 830, the method 800 includes providing one or more spring members between the first plate member and the second plate member. The spring members apply a spring force configured to separate the first plate member from the second plate member. At block 840, the method 800 includes moving the first plate member along a normal axis of the first plate and the second plate to a closed configuration by applying a compressive force that overcomes the spring force and urges an abutment surface of the first plate member against an abutment surface of the second plate member. In the closed configuration a predetermined optical path length is provided through the sample chamber for conducting optical measurements.

In block 830, the method 800 may also include mechanically limiting the predetermined optical path length within a range of +/−1 micron based on a first fixed depth of the chamber into the first plate member relative to the abutment surface of the first plate member and second fixed depth of the chamber into the second plate member relative to the abutment surface of the second plate member. According to aspects of the present disclosure, the method 800 also includes spectroscopically determining the presence of analyte in the sample at block 850 by applying light along the predetermined optical path length.

According to aspects of the present disclosure, the method 800 also includes removing the compressive force after spectroscopically determining the presence of the analyte in the body fluid sample at bloc 860 and allowing the first plate member to be displaced by the spring force along the normal axis away from the second plate member to an open configuration. The method 800 further includes clearing the body fluid sample from the chamber at block 870 while the first plate member is displaced away from the second plate member in the open configuration.

What is claimed is:

1. A method for spectroscopic determination of an analyte in a body fluid sample, the method comprising:
    providing a sample cell having a sample path extending between a first plate member and an opposing second plate member, wherein the sample path is adapted for communicating the body fluid sample from a fluid inlet path through a sample chamber between the first plate member and the second plate member to a fluid outlet path;
    providing one or more spring members between the first plate member and the second plate member, wherein the spring members apply a spring force configured to separate the first plate member from the second plate member; and
    moving the first plate member along a normal axis of the first plate and the second plate to a closed configuration by applying a compressive force that overcomes the spring force and urges an abutment surface of the first plate member against an abutment surface of the second plate member, wherein in the closed configuration a predetermined optical path length is provided through the sample chamber for conducting optical measurements.

2. The method of claim 1, further comprising:
    inserting the body fluid sample into the chamber; and
    spectroscopically determining the presence of the analyte in the sample by applying light along the predetermined optical path length.

3. The method of claim 2, further comprising:
    removing the compressive force after spectroscopically determining the presence of the analyte in the body fluid sample; and,
    allowing the first plate member to be displaced by the spring force along the normal axis away from the second plate member to an open configuration.

4. The method of claim 1 further comprising mechanically limiting the predetermined optical path length within a range of +/−1 based on a first fixed depth of the chamber into the first plate member relative to the abutment surface of the first plate member and second fixed depth of the chamber into the second plate member relative to the abutment surface of the second plate member.

5. The method of claim 1, wherein the analyte is a member selected from the group consisting of hemoglobins, proteins, lipids, and bilirubin.

6. The method of claim 1 further comprising clearing the body fluid sample from the chamber while the first plate member is displaced away from the second plate member in the open configuration.

7. The method of claim 1, wherein the sample cell further comprises a first well portion, wherein the first well portion has a fixed depth relative to the first abutment surface.

8. The method of claim 1, wherein the sample cell further comprises a second well portion, wherein the second well portion has a fixed depth relative to the second abutment surface.

9. The method of claim 1, wherein the sample cell further comprises a first plate member made from an optically clear material and a second plate member made from said optically clear material and opposing the first plate member.

10. The method of claim 1 wherein the spring member is monolithically formed with the first plate member or the second plate member.

* * * * *